United States Patent
Cho et al.

(10) Patent No.: US 6,380,402 B2
(45) Date of Patent: Apr. 30, 2002

(54) PREPARATION OF GAMMA-BUTYROLACTONE BY CATALYTIC HYDROGENATION OF MALEIC ANHYDRIDE

(75) Inventors: Soon-Haeng Cho; Tae-Hwan Kim; Kweon-Ill Kim; Sung-Chul Cho; Jong-Kee Park; Heon-Do Jeong; Hari Chand Bajaj, all of Daejeon-Si (KR)

(73) Assignee: Korea Institute of Energy Research, Daejeon-Si (KR)

( * ) Notice: Subject to any disclaimer, the term of this patent is extended or adjusted under 35 U.S.C. 154(b) by 0 days.

(21) Appl. No.: 09/741,901

(22) Filed: Dec. 22, 2000

(30) Foreign Application Priority Data

Apr. 10, 2000 (KR) .......................................... 2000-18618

(51) Int. Cl.$^7$ ............................................. C07D 307/58
(52) U.S. Cl. ...................................................... 549/325
(58) Field of Search .......................................... 549/325

(56) References Cited

U.S. PATENT DOCUMENTS 5,118,821 A * 6/1992 Dallons et al. ............. 549/325

* cited by examiner

*Primary Examiner*—Bernard Dentz
(74) *Attorney, Agent, or Firm*—Arent Fox Kintner Plotkin & Kahn, PLLC

(57) ABSTRACT

Disclosed is a process for effecting liquid-phase hydrogenation of MAN to GBL in high conversion and high selectivity. The present invention provides an improved process of catalytic hydrogenation for converting MAN or SA to GBL in the liquid phase in the presence of a noble metal (palladium-molybdenum-nickel) catalyst supported on silica having a large surface area. The catalytic hydrogenation is conducted at a temperature of 150 to 250° C. and under a pressure of 50 to 150 kg/cm$^2$.

7 Claims, 1 Drawing Sheet

PREPARATION OF GAMMA-BUTYROLACTONE BY CATALYTIC HYDROGENATION OF MALEIC ANHYDRIDE

BACKGROUND OF THE INVENTION

1. Field of the Invention

The present invention relates to a preparation method of gamma-butyrolactone (GBL) using maleic anhydride (MAN).

2. Description of the Related Art

Current marketability and fair possibility of growth considered, GBL, tetrahydrofuran (THF) and 1,4-butanediol (BDO) are most intriguing substances in the aspect of the industry. A major use of GBL is as a solvent or an intermediate for the pharmaceutical industry. GBL is also used as a feedstock for the production of pyrrolidone, which is used as a solvent for many industrial applications, and a substitute feedstock for pyrrolidone.

The hydrogenation of MAN is comprised of a series of reaction steps. The first step is hydrogenating the double bond (C=C) of MAN to form succinic anhydride (SA) and the subsequent one is hydrogenating the C=O group to yield GBL and THF. The secondary product of the reaction, BDO is directly manufactured from THF, GBL and SA. Byproducts with a chain structure, including alkanes, alcohols and acids are produced from hydrogenolysis of MAN. As well known in the art, the catalytic hydrogenation of MAN leads to various hydrogenated products including SA, GBL, THF and BDO as well as relatively less valuable products such as propanol, butanol and butyric acid.

The catalytic hydrogenation of MAN to GBL is a well-established art for which a great many processes and conditions have been tried to achieve high conversion and high selectivity to GBL with keen interest. However, commercial practice in respect to the production of GBL from MAN has not been entirely successful, especially in terms of high conversion and high selectivity to GBL. These deficiencies usually result from low catalytic activity, byproducts and/or inadequate process conditions, that is, optimally high temperature and pressure.

Dunlop, in U.S. Pat. No. 3,065,243, for example, describes a process in which MAN, SA, or an acid or ester thereof is vaporized and the vapors in hydrogen pass over a reduced copper-chromite catalyst. But, the conversion and selectivity to GBL are relatively low. Kyowa, in U.K. Patent No. 1,168,220 discloses that a reduced copper-zinc-chromium catalyst can be used in place of the copper-chromite catalyst but with only marginally improved results.

Miya, in U.S. Pat. No. 3,580,930, employs a copper-zinc-chromium catalyst with an at most 50% selectivity to GBL.

Attig, in EPA 332,140, describes hydrogenation for converting MAN to THF and GBL in the presence of a copper-zinc-chromium-alumina catalyst with an at most 50% selectivity to GBL.

U.S. Pat. No. 3,312,718 discloses a conversion of SA to GBL in the presence of a Ni-based hydrogenation catalyst along with silicotungastic acid as a promoter. U.S. Pat. No. 3,113,138 discloses a conversion of SA to GBL using a palladium catalyst in the liquid phase. However, these processes adversely lead to problems in regard to short lifetime of the catalysts and low yields of the products.

Canadian Pat. No. 1,041,529 describes a liquid-phase conversion of MAN to GBL using an oxide-palladium-silica catalyst with high conversion and high selectivity to GBL. But, this process inevitably requires high temperature and high pressure, for example, 250° C. and 150 kg/cm$^2$ and its practice in the industry gives rise to a demand of delicate and expensive facility.

Many catalyst modifications used in hydrogenation of SA to GBL are disclosed in other patents including U.S. Pat. No. 4,620,017. However, the processes using these catalysts inevitably require a step of separating the used catalyst in order to use another fresh catalyst, since SA obtained from conversion of MAN has to be separated prior to a second hydrogenation.

In commercial operation using these and other processes, as described above, the catalysts and process conditions employed have been found to be unsatisfactory, usually because the catalyst is deactivated through tar or coke formation within a relatively short time. The short lifetime of the catalysts also makes it virtually impossible to carry on a production run for a prolonged period of time. Thus developing catalysts and process conditions to achieve high conversion to GBL in a single step under adequate process conditions is of great importance in the aspects of both technology and economy.

SUMMARY OF THE INVENTION

Accordingly, it is an object of the present invention to provide a process for effecting liquid-phase hydrogenation of MAN to GBL in high conversion and high selectivity.

It is another object of the present invention to provide a process for effecting hydrogenation with a relatively low pressure, and a novel catalyst for carrying out the hydrogenation with high catalytic activity and high selectivity.

The process of this invention is very useful in the aspect of economy because conversion of MAN to GBL can be achieved in a simple reaction step and the catalyst used is stable to the reaction, i.e., retarded in deactivation, thus prolonging the lifetime, and can be recycled several times. Examples of the suitable catalyst include activated catalysts, such as palladium-molybdenum-nickel catalyst, palladium-ruthenium-nickel catalyst, or palladium-ruthenium-nickel catalyst supported on silica having a large surface area.

The present invention is directed to a liquid phase process for converting MAN to GBL in the presence of a palladium-molybdenum-nickel catalyst supported on silica that has a large surface area. The process of this invention is typically carried out at elevated temperature and pressure, for example, in the range of 100 to 275° C. and 50 to 150 kg/cm$^2$, dominantly in the range of 150 to 230° C. and 50 to 100 kg/cm$^2$. FIG. 1 shows the procedure for preparing GBL. This process employs an autoclave, which is operated in a batch mode or a continuous mode. First, MAN and THF are introduced as a feedstock into the autoclave and the resulting products are separated from the catalyst to yield GBL. The GBL is then subjected to a qualitative analysis on the HPLC and GC columns.

The base material for the preparation of the catalyst is preferably a solution containing metal salts, which are soluble in water and readily decomposed in the metal form by calcination and reduction and include: nickel salts such as nickel nitrate, nickel formate, nickel acetate, or nickel salts of other volatile organic acids; palladium salts such as palladium chloride, palladium acetate, or palladium amine complex; and molybdenum salts such as ammonium molybdate tetrahydrate, molybdenum acetate, or molybdenum oxychloride.

Preferably, silica used as a carrier has a large specific surface area in the range of more than 100 to 500 m$^2$/g. The use of silica whose specific surface area is less than 50 m²/g results in considerably low conversion and selectivity to GBL.

A sufficient amount of the catalyst is prepared from silica carrier, nickel salt solution, palladium salt solution and molybdenum salt solution with the composition as follows:

Nickel: 20–35 wt. %;
Palladium: 1–4 wt. %;
Molybdenum: 2–8 wt. %; and
Silica: for the rest in percentage The catalysts are generally used in the form of powder or pellets. The exemplary palladium-molybdenum-nickel catalyst as used herein is supported on a carrier or in an immersion or suspension of the carrier.

In contrast to other processes for converting MAN to GBL that are conducted in the vapor phase, the process of this invention is carried out in the liquid phase which is a great advantage with regard to conversion and reactor dimensions. The liquid phase process is characterized in that the feedstock is not overheated and hence no deterioration of the catalytic activity due to coke formation. The catalytic process can be conducted in a wide range of inert solvents, for example, aromatics such as benzene, toluene or xylene; aliphatic alcohols such as methanol, ethanol or higher alcohols; dimethylformamide; and cyclic ethers such as THF or dioxane. A particularly preferred solvent for the conversion of MAN is GBL, which is the end product of the process and thus needs not be removed. The conversion and selectivity to GBL are the same whether GBL or another solvent is used in the course of the reaction. For the same reason, THF is also usable as a solvent in the conversion of GBL to THF. Preferably, the MAN concentration in the solvent is variable from 30 to 60 wt. % and the amount of the catalyst is approximately 1 to 20 wt. % based on the weight of MAN.

The process of this invention is conducted at a temperature in the range of 200 to 240° C. under the pressure of 50 to 100 kg/cm². The process can also be conducted at a temperature below 200° C., in which case the reaction rate is excessively low so that it takes too much time to achieve high conversion to GBL. If the reaction temperature is raised to above 240° C., the yield of byproducts increases. This problem can be solved through reduction of the reaction time. Optimum temperature and pressure conditions contribute to the enhanced quality of the end product, GBL.

The process of this invention provides high selectivity to GBL in the range of 94 to 98% depending on the reaction time and high conversion of MAN to GBL in the range of 90 to 100%. The reaction time is variable between 1.5 and 8 hours based on the experimental conditions, and preferably in practice between 1.5 and 3 hours.

DETAILED DESCRIPTION OF THE PREFERRED EMBODIMENT

Figure 1:
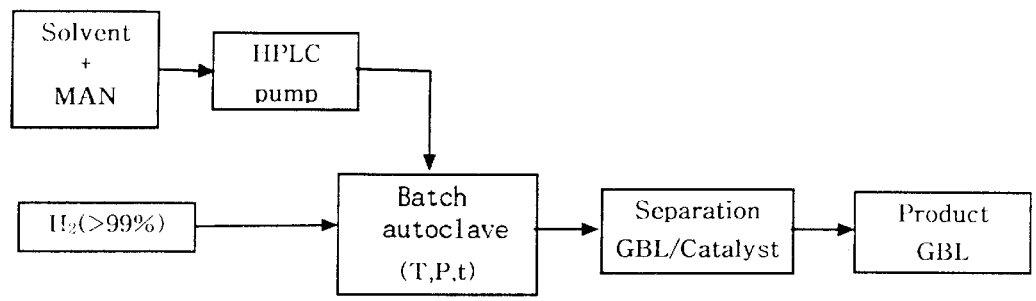
FIG. 1 is a flow chart showing a process for preparing GBL.

The following examples are presented in order to more fully illustrate the nature of the present invention and the manner of practicing the same. In these examples, the best mode contemplated for carrying out this invention is set forth.

Those particular examples that will be described later are concluded to the following entire example.

A process for preparing gamma-butyrolactone from maleic anhydride by addition of hydrogen in the liquid phase is conducted in the presence of a palladium-molybdenum-nickel catalyst supported on silica having a specific surface area of at least 50 m²/g at a temperature in the range of 150 to 250° C. and under a pressure of 50 to 150 kg/cm². The catalyst of this process includes, based on the total weight of the catalyst, about 40 to 70 wt. % of silica, 15 to 40 wt. % of nickel, 1 to 4 wt. % of palladium and 2 to 8 wt. % of molybdenum.

The catalyst comprising palladium, molybdenum, nickel and silica is prepared by coprecipitation or multi-stage impregnation, which method is well known in the art and will not be described herein.

Preferably, the mole ratio of palladium to molybdenum in the catalyst is 0.5: 2.0. Both tetrahydrofuran and gamma-butyrolactone are added as a solvent to the maleic anhydride. Alternatively, no solvent is added to the maleic anhydride. The amount of the catalyst is preferably in the range of 0.5 to 30 wt. % based on the weight of the maleic anhydride.

EXAMPLE 1

Catalyst A supported on silica was prepared with the composition as follows: 2.36 wt. % of palladium, 4.53 wt. % of molybdenum and 24.76 wt. % of nickel. 10 g of the catalyst A prepared above was added to 60 g of MAN and 240 g of THF (solvent). The reaction mixture was then packed into a 1 l autoclave and kept under stirring at a raised temperature of 235° C. for 3 hours to maintain the pressure of the autoclave at 90 kg/cm². After 3 hours of the reaction, the reaction mixture was cooled to the room temperature and depressurized. With the catalyst filtered out, the filtrate was analyzed on the GC and HPLC columns. The analysis showed that the process of this example led to a 98 percent conversion of MAN with the yields of 96.4% for GBL, 2.2% for SA and 1.4% for byproducts.

EXAMPLE 2

Catalyst A supported on silica was prepared with the composition as follows: 2.36 wt. % of palladium, 4.53 wt. % of molybdenum and 24.76 wt. % of nickel. 10 g of the catalyst A prepared above was added to 60 g of MAN and 240 g of THF (solvent). The reaction mixture was then packed into a 1 l autoclave. Following the introduction of hydrogen gas with the pressure of 50 kg/cm², the reaction mixture was kept under stirring at a raised temperature of 220° C. for 3.5 hours to maintain the pressure of the autoclave at 80 bar. After 3.5 hours of the reaction, the reaction mixture was cooled to the room temperature and depressurized. With the catalyst filtered out, the filtrate was analyzed on the GC and HPLC columns. The analysis showed that the process of this example led to a 96 percent conversion with the yields of 92.4% for GBL, 5.6% for SA and 2% for byproducts.

EXAMPLE 3

Catalyst B supported on silica was prepared with the composition as follows: 2 wt. % of palladium, 2 wt. % of molybdenum and 25 wt. % of nickel. 10 g of the catalyst B prepared above was added to 60 g of MAN and 250 ml of THF (solvent). The reaction mixture was then packed into a 1 l autoclave and kept under stirring at a raised temperature of 245° C. for 5 hours to maintain the pressure of the autoclave at 60 kg/cm². After 5 hours of the reaction, the reaction mixture was cooled to the room temperature and depressurized. With the catalyst filtered out, the filtrate was analyzed on the GC and HPLC columns. The analysis showed that the process of this example led to a 100 percent conversion with the yields of 95.7% for GBL and 4.3% for SA.

EXAMPLE 4

Catalyst C supported on silica was prepared with the composition as follows: 2 wt. % of palladium, 2 wt. % of molybdenum and 0 wt. % of nickel. 10 g of the catalyst C prepared above was added to 60 g of MAN and 200 ml of THF (solvent). The reaction mixture was then packed into a 1 l autoclave. Following the introduction of hydrogen gas with the pressure of 50 kg/cm$^2$, the reaction mixture was kept under stirring at a raised temperature of 240° C. for 3.5 hours to maintain the pressure of the autoclave at 85 bar. After 3.5 hours of the reaction, the reaction mixture was cooled to the room temperature and depressurized. With the catalyst filtered out, the filtrate was analyzed on the GC and HPLC columns. The analysis showed that the process of this example led to a 99.8% conversion with the yields of 57.3% for GBL, 42.6% for SA and 0.2% for byproducts.

EXAMPLE 5

Figure 2:
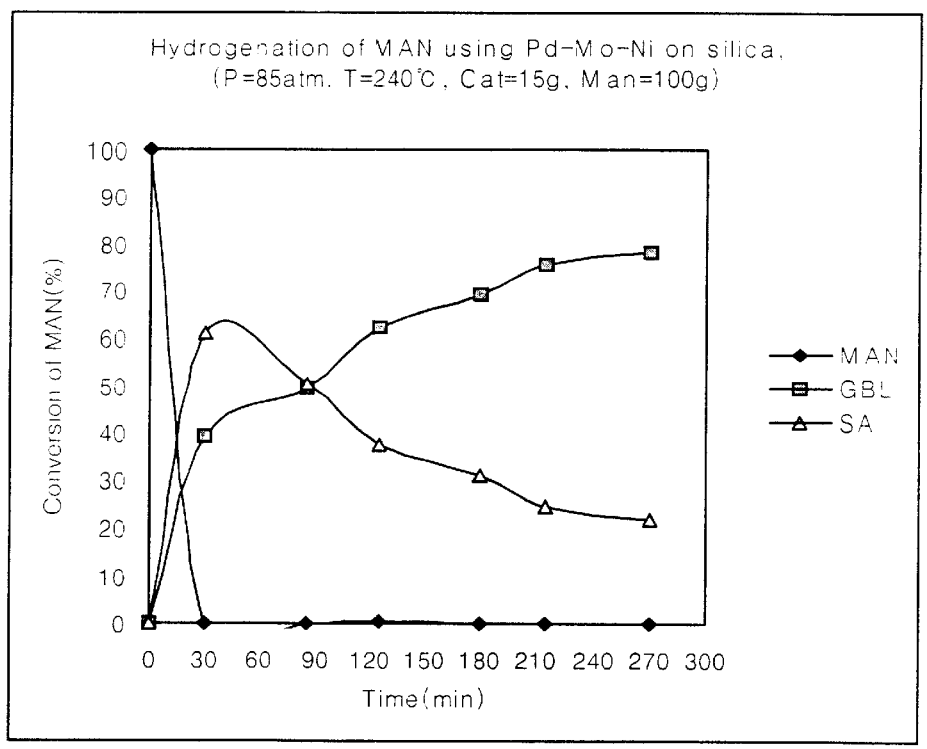
FIG. 2 is a graph plotting the conversions of MAN, SA and GBL based on the reaction time.

Catalyst D supported on silica was prepared with the composition as follows: 1.5 wt. % of palladium, 3 wt. % of molybdenum and 20 wt. % of nickel. 10 g of the catalyst D prepared above was added to 300 g of MAN without THF (solvent) at 80° C. The reaction mixture was then packed into a 1 l autoclave. Following the introduction of hydrogen gas with the pressure of 50 kg/cm$^2$, the reaction mixture was kept under stirring at a raised temperature of 245° C. for 6 hours to maintain the pressure of the autoclave at 70 bar. After 6 hours of the reaction, the reaction mixture was cooled to the room temperature and depressurized. With the catalyst filtered out, the filtrate was analyzed on the GC and HPLC columns. The analysis showed that the process of this example led to a 100% conversion with the yields of 82.2% for GBL and 17.86% for SA. For example, FIG. 2 shows the conversion to the products based on the reaction time.

The invention has been described in detail with particular reference to preferred embodiments thereof, but it will be understood that variations and modifications can be effected within the spirit and scope of the invention.

The present invention provides an improved process of catalytic hydrogenation for converting MAN or SA to GBL in the liquid phase in the presence of a noble metal (palladium-molybdenum-nickel) catalyst supported on silica having a large surface area. As such, the invention provides a novel catalyst with high activity and selectivity to GBL that is a useful feedstock for the preparation of pyrrolidone, which is used as a solvent in many industrial applications, and a substitute material for pyrrolidone.

References

1. U.S. Pat. No. 3,065,243 (November, 1962).
2. U.S. Pat. No. 3,580,930 (May, 1971)
3. U.S. Pat. No. 3,312,718
4. U.S. Pat. No. 3,113,138
5. U.S. Pat. No. 4,620,017, "Catalytic hydrogenation of succinic anhydride to butyrolactone"
6. U.K. Pat. No. 1,168,220 (October, 1969)
7. Canadian Pat. No. 1,041,529, "Process for the production of gamma-butyrolactone and novel catalyst therefore"
8. EPA 332,140 (June, 1989)

What is claimed is:

1. A process for preparing gamma-butyrolactone from maleic anhydride by addition of hydrogen in the liquid phase, wherein the process is conducted in the presence of a palladium-molybdenum-nickel catalyst supported on silica having a specific surface area of at least 50 m$^3$/g at a temperature in the range of 150 to 250° C. and under a pressure of 50 to 150 kg/cm$^2$.

2. The process as claimed in claim 1, wherein the catalyst comprises, based on the total weight of the catalyst, about 40 to 70 wt. % of silica, 15 to 40 wt. % of nickel, 1 to 4 wt. % of palladium and 2 to 8 wt. % of molybdenum.

3. The process as claimed in claim 1, wherein the catalyst comprising palladium, molybdenum, nickel and silica is prepared by coprecipitation or multi-stage impregnation.

4. The process as claimed in claim 1, wherein the mole ratio of palladium to molybdenum in the catalyst is 0.5:2.0.

5. The process as claimed in claim 1, wherein tetrahydrofuran and gamma-butyrolactone are added as a solvent to the maleic anhydride.

6. The process as claimed in claim 1, wherein no solvent is added to the maleic anhydride.

7. The process as claimed in claim 1, wherein the amount of the catalyst is 0.5 to 30 wt. % based on the weight of the maleic anhydride.

* * * * *